(12) United States Patent
Palmieri

(10) Patent No.: US 9,995,377 B2
(45) Date of Patent: Jun. 12, 2018

(54) DEVICE FOR CONVERTING A ROTATING MOTION INTO A RECIPROCATING MOTION AND AN ELECTRIC MASCARA APPLICATOR ASSEMBLY HAVING SUCH A DEVICE

(71) Applicant: Herman David Palmieri, Pittsburgh, PA (US)

(72) Inventor: Herman David Palmieri, Pittsburgh, PA (US)

(*) Notice: Subject to any disclaimer, the term of this patent is extended or adjusted under 35 U.S.C. 154(b) by 906 days.

(21) Appl. No.: 13/860,212

(22) Filed: Apr. 10, 2013

(65) Prior Publication Data

US 2013/0269457 A1 Oct. 17, 2013

Related U.S. Application Data

(60) Provisional application No. 61/686,819, filed on Apr. 12, 2012.

(51) Int. Cl.
| | |
|---|---|
| *A61C 17/34* | (2006.01) |
| *A46B 13/02* | (2006.01) |
| *A45D 40/26* | (2006.01) |
| *F16H 25/12* | (2006.01) |
| *A61C 17/16* | (2006.01) |

(52) U.S. Cl.
CPC ........... *F16H 25/122* (2013.01); *A45D 40/26* (2013.01); *A45D 40/265* (2013.01); *A46B 13/02* (2013.01); *A46B 13/023* (2013.01); *A61C 17/16* (2013.01); *A61C 17/349* (2013.01); *F16H 25/12* (2013.01); *A45D 2200/207* (2013.01); *A46B 2200/1053* (2013.01); *A61C 17/3436* (2013.01); *A61C 17/3445* (2013.01); *Y10T 74/18312* (2015.01)

(58) Field of Classification Search
CPC .... A46B 13/02; A46B 13/023; A61C 17/3445
USPC ....................... 30/44, 45, 392, 393
See application file for complete search history.

(56) References Cited

U.S. PATENT DOCUMENTS

| | | | | |
|---|---|---|---|---|
| 3,451,086 A | * | 6/1969 | Burgett | A61C 17/26 119/609 |
| 3,588,936 A | * | 6/1971 | Duve | A61C 17/3472 15/22.1 |
| 3,984,890 A | * | 10/1976 | Collis | A46B 9/045 15/22.1 |

(Continued)

FOREIGN PATENT DOCUMENTS

| | | | |
|---|---|---|---|
| EP | 2 441 346 | * | 4/2012 |
| FR | 1 166 163 | * | 11/1958 |

*Primary Examiner* — Randall Chin

(57) ABSTRACT

A device for converting a rotating motion into a reciprocating motion comprises a motor having a rotatable motor shaft carrying cylindrical component, an embedded cam groove of the cylindrical component, a rod component constrained to travel back and forth and forth, and a cam follower carried on the rod component. The cam follower is engaged in the embedded cam groove track of the cylindrical component so that as the rotatable motor shaft rotates, the cam follower transmits the movement dictated by the embedded cam groove track profile thereby causing the rod component to travel back and forth once for each rotation of rotatable motor shaft. There is also disclosed a mascara applicator assembly; a first electric toothbrush assembly; and a second electric toothbrush assembly comprising such a device.

17 Claims, 15 Drawing Sheets

(56) References Cited

U.S. PATENT DOCUMENTS

| | | | | |
|---|---|---|---|---|
| 4,991,298 A | * | 2/1991 | Matre | A01G 3/08 30/166.3 |
| 5,607,265 A | * | 3/1997 | Lane | B23D 51/16 144/35.2 |
| 8,176,590 B1 | * | 5/2012 | Brar | A46B 5/0012 15/167.1 |
| 2004/0049868 A1 | * | 3/2004 | Ng | A61C 17/34 15/22.2 |
| 2012/0124758 A1 | * | 5/2012 | Sabisch | A46B 13/02 15/21.1 |

* cited by examiner

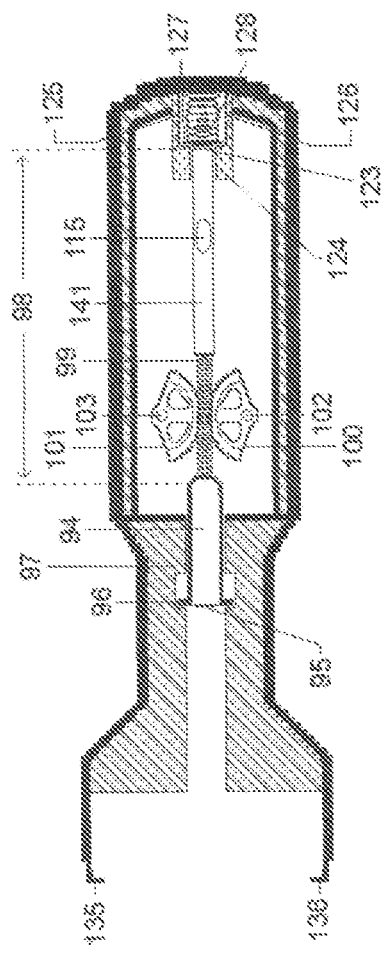
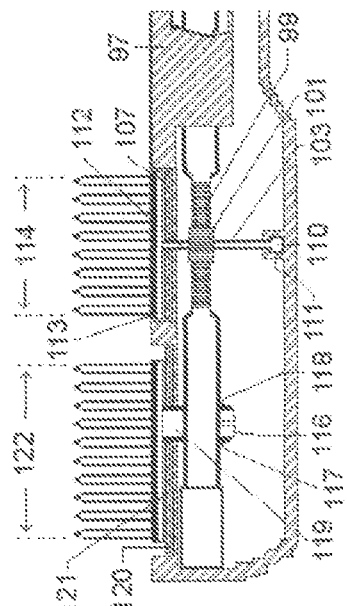
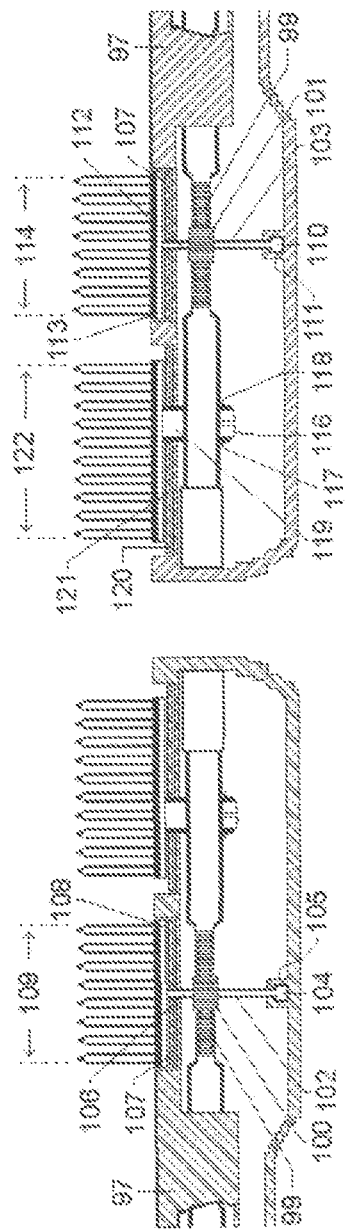

DEVICE FOR CONVERTING A ROTATING MOTION INTO A RECIPROCATING MOTION AND AN ELECTRIC MASCARA APPLICATOR ASSEMBLY HAVING SUCH A DEVICE

This application claims priority to the U.S. Provisional application No. 61/686,819 filed on Apr. 12, 2012.

BACKGROUND OF THE INVENTION

Many mechanical assemblies such as internal combustion or steam engines and cutting or stamping machines convert a relating motion into a reciprocating motion or a reciprocating motion into a rotating motion. Although cranks and crankshafts are ideal in these large assemblies they become cumbersome and inconvenient when applied to any small hand-held devices especially a mascara applicator. Therefore, there is a need for a compact, lightweight mechanism to achieve the converting a rotating motion into a reciprocating motion for use in small hand-held devices.

FIELD OF THE INVENTION

The present invention relates to a device for converting a rotating motion into a reciprocating motion for use, for example, in an electric mascara applicator assembly and in an electric toothbrush assembly having such a device. However, the present invention is not limited to minute devices.

SUMMARY OF THE INVENTION

The present invention proposes a device for converting a rotating motion into a reciprocating motion; an electric mascara applicator assembly having such a device; a first electric toothbrush assembly having such a device and a second toothbrush assembly having such a device.

According to a first aspect of the present invention there is provided a device for converting a rotating motion into a reciprocating motion comprising:

a rotatable motor shaft carrying a cylindrical component having an embedded cam groove therein;
  a rod component constrained to travel back and forth; and
  a cam follower carried on said rod component for engagement in said embedded cam groove of said cylindrical component so that as said rotatable motor shaft rotates, the said cam follower transmits the movement dictated by the embedded cam groove profile to said rod component thereby causing the said rod component to travel back and forth once for each rotation of said rotatable motor shaft.

According to the second aspect of the present invention there is provided a mascara applicator assembly comprising the said device defined above.

According to the third aspect of the present invention there is provided a first electric toothbrush assembly comprising the said device defined above.

According to the fourth aspect of the present invention there is provided a second electric toothbrush assembly comprising the said device defined above.

An advantage of one or more of the embodiments of the present invention is that the conversion of the rotating motion into a reciprocating motion is in its simplest form. Thereby, the mechanism is simple to construct and may be used in small device such as said above assemblies.

BRIEF DESCRIPTION OF THE DRAWINGS

For the sake of illustration the preferred features of the invention will now be described with reference to the following figures in which:

FIG. 27 is an upper partial cross-sectional top view of the electric toothbrush having a detachable head assembly.

FIG. 28 is an upper partial cross-sectional right side view of the electric toothbrush having a detachable head assembly.

FIG. 29 is an upper partial cross-sectional left side view of the electric toothbrush having a detachable head assembly.

DETAILED DESCRIPTION OF PREFERRED EMBODIMENTS

Figure 1:
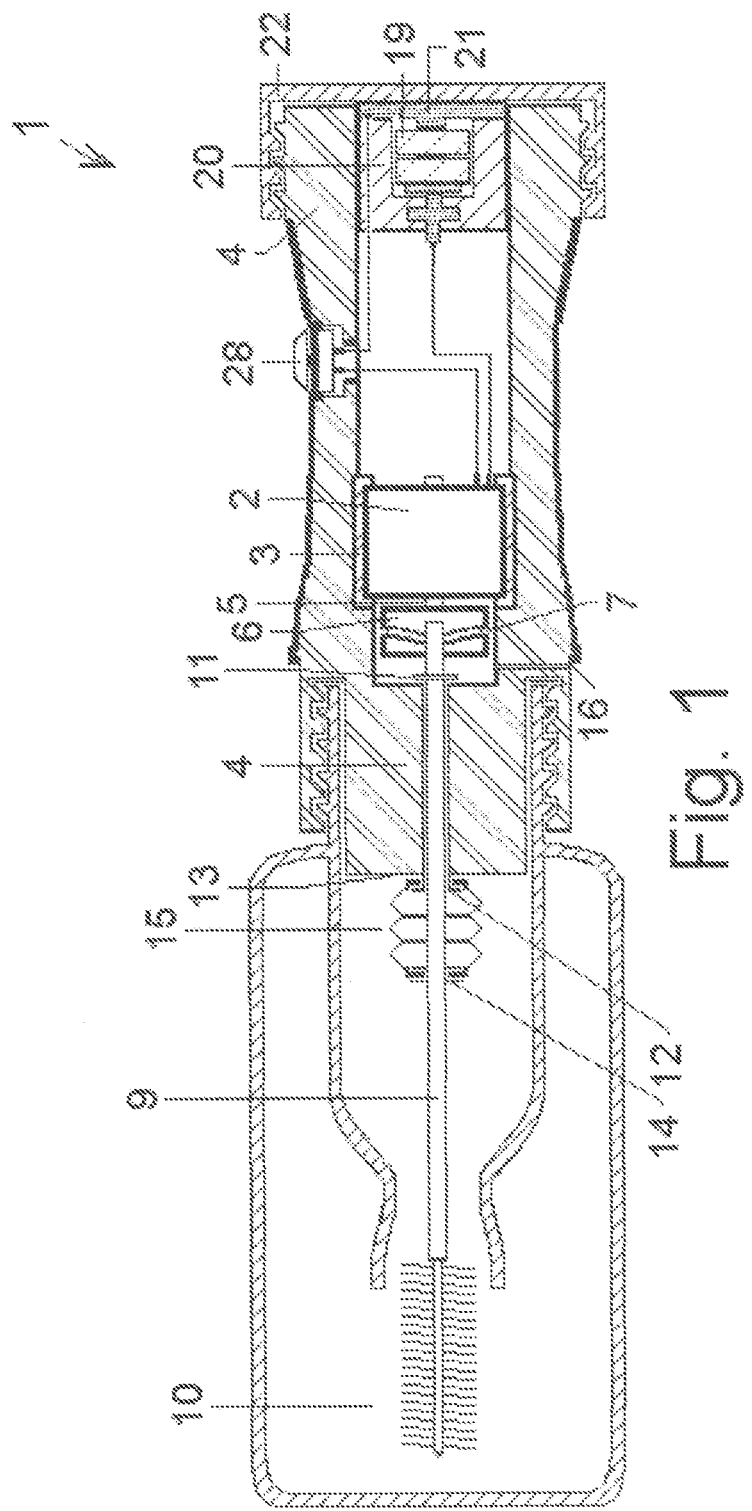
FIG. 1 is a cross-sectional view of the mascara applicator assembly including a reciprocating drive mechanism according to an embodiment of the invention.
Figure 4:
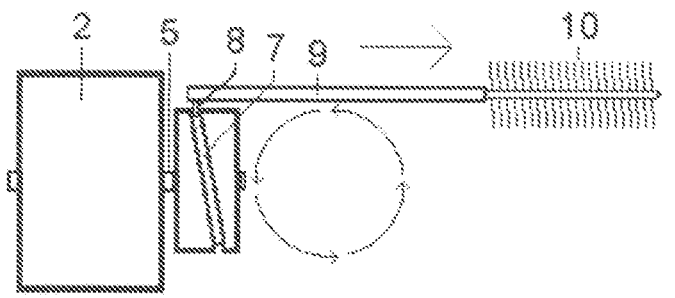
FIG. 4 is a first progressive view of a reciprocating drive mechanism of the mascara applicator assembly in operation.

FIG. 1 shows an electric mascara applicator assembly 1 which further comprises a DC motor 2 encased in a motor housing 3. Motor housing 3 is embedded in housing 4. The DC motor 2 includes rotatable motor shaft 5 on which cylindrical wheel 6 is attached. The cylindrical wheel 6 has an embedded cam groove track 7 in which a cam follower pin 8 is loosely seated, as shown in FIG. 4. The cam follower pin 8 is attached to a reciprocating push-pull rod 9, as shown in FIG. 4. Brush head 10, as shown in FIG. 1, is attached to the other end of reciprocating push-pull rod 9. A portion of the reciprocating push-pull rod 9 is constrained by a portion of housing 4 thereby constraining the movement of the entire reciprocating push-pull rod 9. A flat circular stop limiter 11 is attached to the reciprocating push-pull rod 9 in the event of an internal mechanical malfunction involving said push-pull rod 9 would occur and has no other purpose. The bellows expansion seal seat 12 is attached to the outer bottom housing 13. The bellows expansion seal seat 14 is attached to the reciprocating push-pull rod 9. The bellows expansion seal 15 is seated in bellows expansion seal seat 12 and bellows expansion seal seat 14. Air vent 16 is embedded in housing 4, as shown in FIG. 1.

Figure 2:
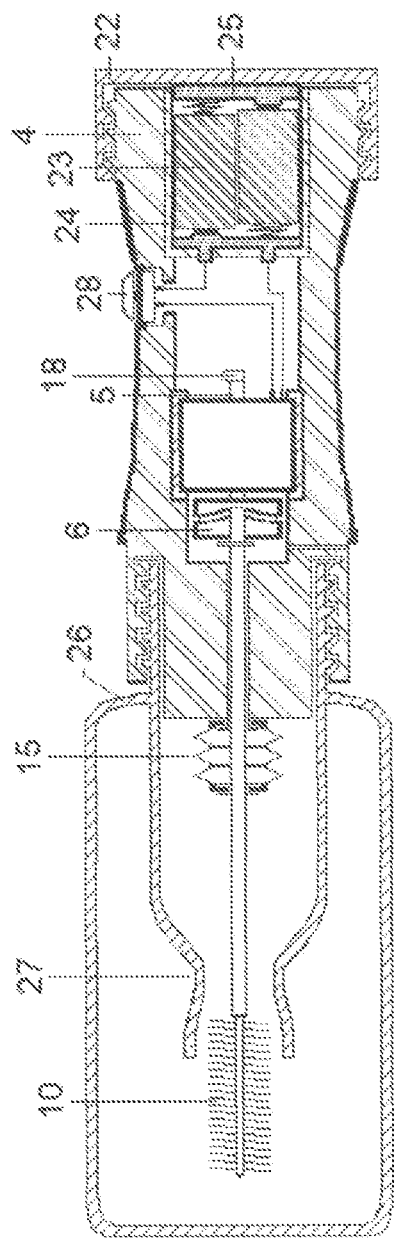
FIG. 2 is a cross-sectional view of the mascara applicator assembly including a reciprocating drive mechanism according to an embodiment of the invention showing a different battery type.
Figure 3:
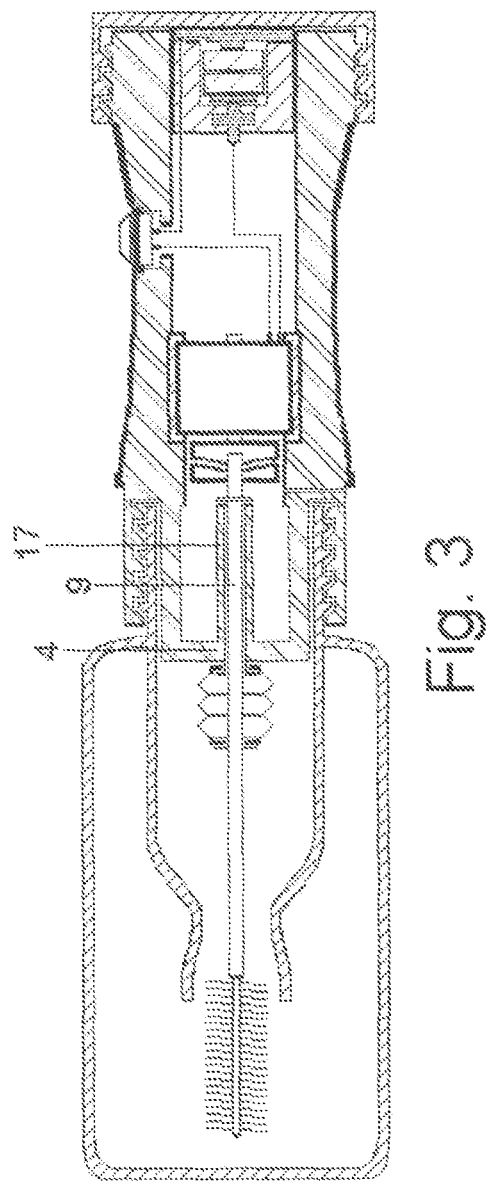
FIG. 3 is a cross-sectional view of the mascara applicator assembly including a reciprocating drive mechanism according to an embodiment of the invention showing a tube to constrain a rod component.

The reciprocating push-pull rod 9 may be constrained by a tube 17 retained within the housing 4, as shown in FIG. 3. At the other end of the rotatable motor shaft 5 to that carrying the cylindrical wheel 6, an optional weight 18, as shown in FIG. 2, may be attached. As shown in FIG. 1, batteries 19 rest within battery compartment 20 which is embedded in housing 4. Removable negative battery contact 21 is held firmly in place by end cap 22. As shown in FIG. 2, batteries 23 rest within battery compartment 24 which is embedded in housing 4. Removable positive and negative battery contact 25 is held firmly in place by end cap 22. Mascara applicator assembly 1 further composes detachable cosmetic tank 26 which is designed to distribute mascara evenly upon brush 10 when brush 10 is removed from cosmetic tank 26 by brush 10 being pulled through trimmer 27.

The DC motor 2 is driven by one or more batteries 19, as shown in FIG. 1 or another type of primary batteries 23, as shown in FIG. 2. The DC motor 2 is driven by one or more batteries 19, as shown in FIG. 1 or another type of primary batteries 23, as shown in FIG. 2. DC motor 2 may be powered by a battery pack, which may be of the lithium-ion type for ready charging via a secondary voltage coil and an integral male socket portion within housing 4, not shown. Said male socket portion is detachably received in a corresponding female socket portion provided in a charger base assembly having a primary charging coil, also not shown. The electrical circuit would be defined with one side of the secondary coil attached to a negative battery terminal connector and the other side of the secondary coil coupled through a diode to the positive battery terminal. The diode rectifies voltage out-puts from the coil, also not shown. Other prior art charging circuitry may be used. DC motor 2 is controlled by an on-off switch 28.

In operation, the user starts the DC motor by moving the on-off switch 28 to the on position. As the cylindrical wheel 6 that is mounted on rotatable motor shaft 5 is rotated by the DC motor 2, the cam follower pin 8 follows the groove of the embedded cam groove track 7 to produce the desired back and forth motion of the reciprocating push-pull rod 9. The shape of the embedded cam groove track 7 defines the distance that the reciprocating push-pull rod 9 and the attached brush head 10 travel back and forth. As the reciprocating push-pull rod 9 travels forth the bellows expansion seal 15 expands, as shown in FIG. 1, and as the reciprocating push-pull rod travels back the bellows expansion seal 15 contracts, as shown in FIG. 2. The bellows expansion seal 15 maintains the seal of the opening between the reciprocating push-pull rod 9 and the opening of that portion of housing 4 that constrains the reciprocating push-pull rod 9. Air vent 16 provides a means for air to flow freely during the expansion and contraction of the bellows expansion seal 15.

Figure 5:
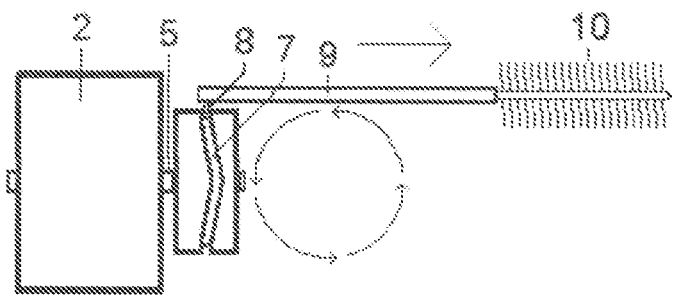
FIG. 5 is a second progressive view of a reciprocating drive mechanism of the mascara applicator assembly in operation.
Figure 6:
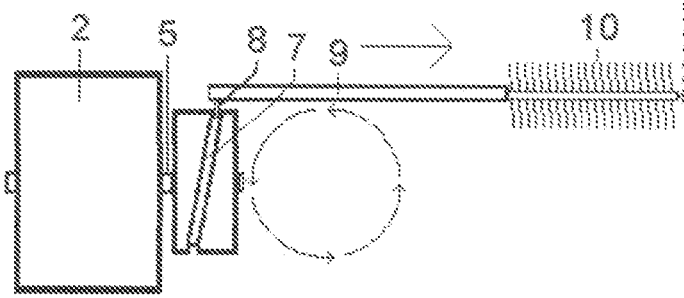
FIG. 6 is a third progressive view of a reciprocating drive mechanism of the mascara applicator assembly in operation.
Figure 7:
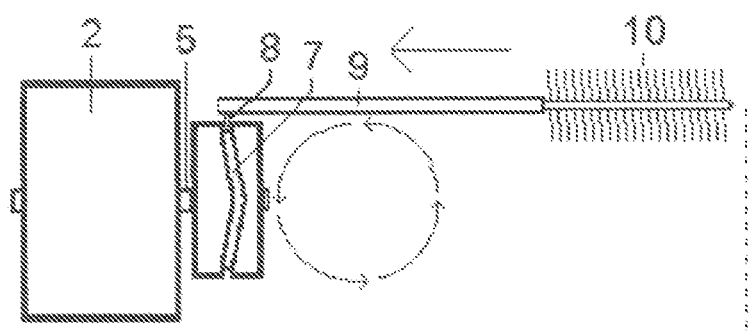
FIG. 7 is a fourth progressive view of a reciprocating drive mechanism of a mascara applicator assembly in operation.
Figure 8:
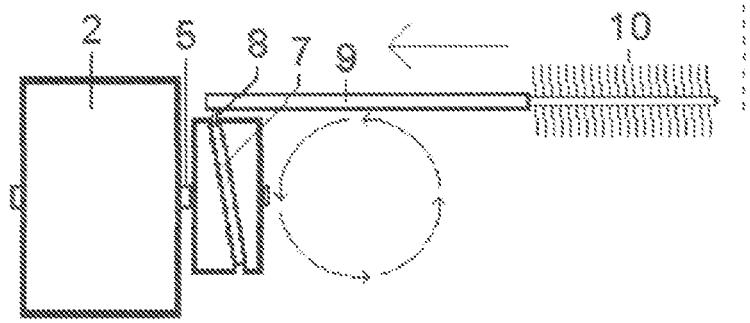
FIG. 8 is a fifth progressive view of a reciprocating drive mechanism of a mascara applicator assembly in operation.

A partial progressive sequence of events illustrating one complete cycle of the reciprocating drive mechanism for an electric mascara applicator assembly 1 of the type shown in FIG. 1 is shown in FIGS. 4, 5, 6, 7 and 8. In FIGS. 4, 5, 6, 7 and 8 DC motor 2 is rotating the rotatable motor shaft 5 counterclockwise. In FIG. 4 the embedded cam groove track 7 is at its closest point to casing surface of DC motor 2. As the rotatable motor shaft 5 rotates counterclockwise, the cam follower pin 8 follows the groove of the embedded cam groove track 7 and causes the reciprocating push-pull rod 9 and brush head 10 to travel forth, as shown in FIG. 5 until it reaches the furthest forward plotted distance of the reciprocating push-poll rod 9, as shown in FIG. 6. As the rotatable motor shaft 5 continues to rotate the direction of the reciprocating push-pull rod 9 is changed to the opposite or back direction, as shown in FIG. 7, until it reaches that point where once again the embedded cam groove track 7 is at its closest point to casing surface of DC motor 2, as shown in FIG. 8. This cycle is continually repeated until the on-off switch 28 is moved by the user to the off position. The short back and forth movement of brush head 10 aids the uses in the application of mascara to the desired eyelash, not shown.

Optional weight 18, as shown in FIG. 2 produces an off-centered rotation when rotatable motor shaft 5 rotates causing a vibration to occur that in some instance may aid the user in the application of mascara.

Figure 9:
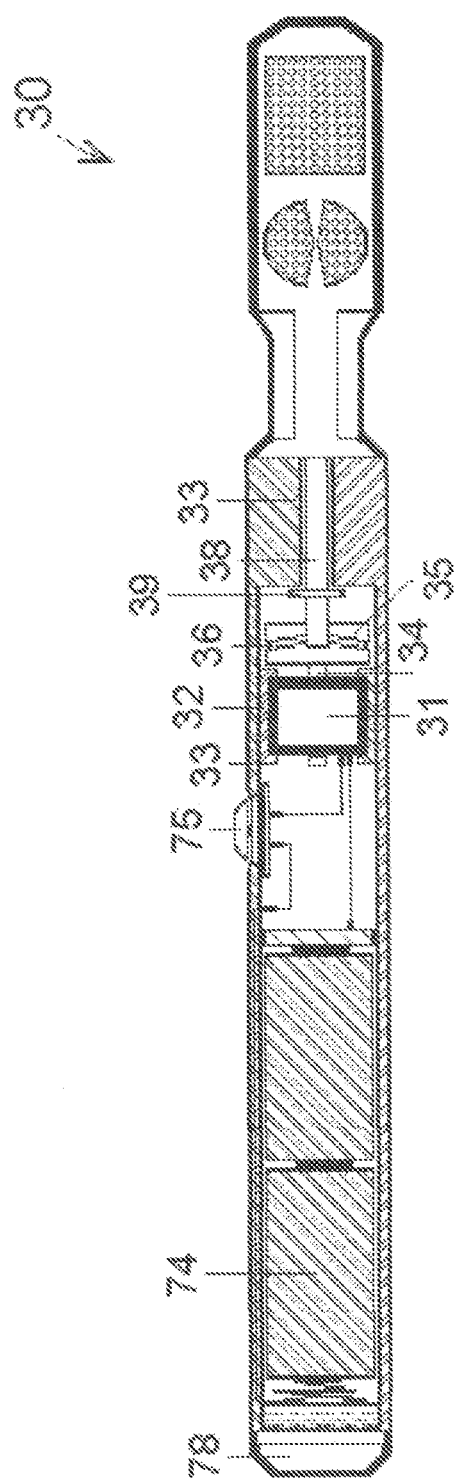
FIG. 9 is a partial cross-sectional top view of the electric toothbrush assembly including a reciprocating drive mechanism according to an embodiment of the invention.
Figure 10:
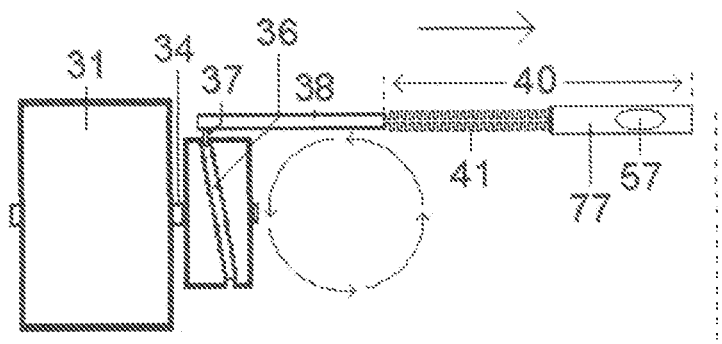
FIG. 10 is a first progressive view of a reciprocating drive mechanism of the electric toothbrush assembly in operation.
Figure 15:
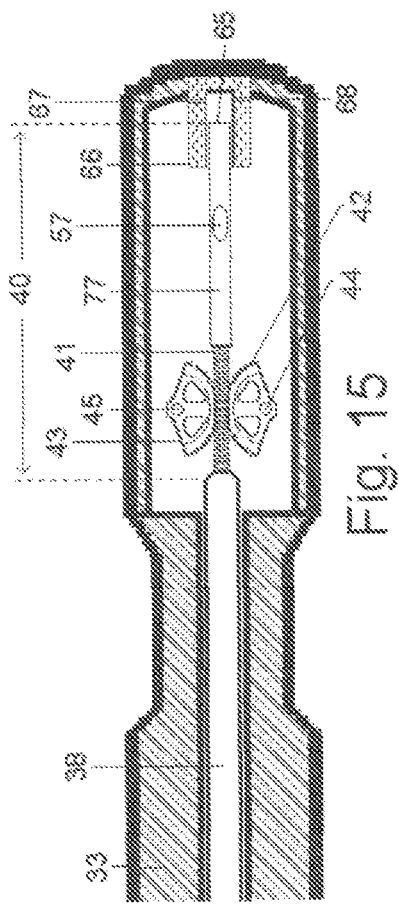
FIG. 15 is an upper partial cross-sectional top view of the electric toothbrush assembly.
Figure 17:
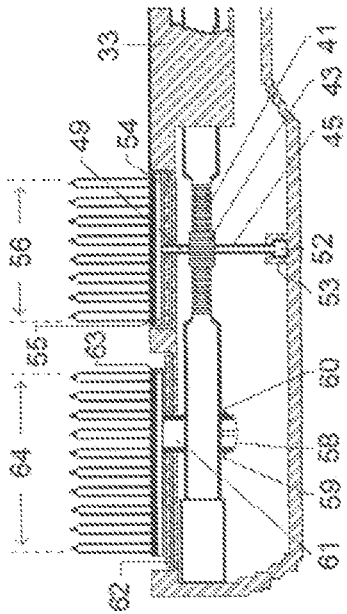
FIG. 17 is an upper partial cross-sectional left side view of the electric toothbrush assembly.
Figure 16:
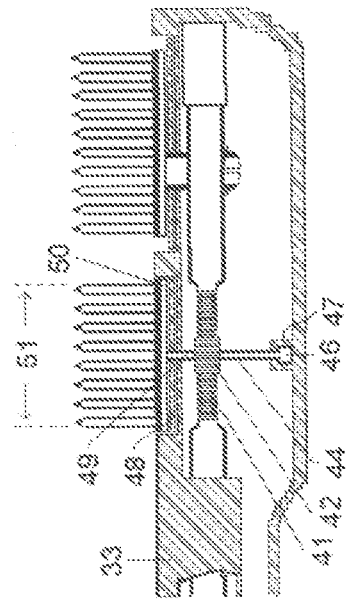
FIG. 16 is an upper partial cross-sectional right side view of the electric toothbrush assembly.

FIG. 9 shows a first electric toothbrush assembly 30 which comprises a DC motor 31 encased in a motor housing 32. Motor housing 32 is embedded in housing 33. The DC motor 31 includes rotatable motor shaft 34 or which cylindrical wheel 35 is attached. The cylindrical wheel 35 has an embedded cam groove track 36 in which a cam follower pin 37 is loosely seated, as shown in FIG. 10. The cam follower pin 37 is attached to a reciprocating push-pull rod 38, as shown in FIG. 10. A portion of the reciprocating push-pull rod 38 is constrained by a portion of housing 33 thereby constraining the movement of the entire reciprocating push-pull rod 38, as shown in FIG. 9. A flat circular stop limiter 39 is attached to the reciprocating push-pull rod 38. Guide rod 40 is attached at the other end of reciprocating push-pull rod 38 to that to which the cam follower pin 37 is attached, as shown in FIG. 15. Guide rod 40 comprises a geared shaft 41 which simultaneously engages first semi gear wheel 42 and second semi gear wheel 43. First semi gear wheel 42 and second semi gear wheel 43 is attached to first shaft 44 and second shaft 45 respectively, as shown in FIG. 15. Shaft 44 extends in opposite directions from its attachment to first semi gear wheel 42, as shown in FIG. 16. First rotating anchor end 46 of shaft 44 rest in extended housing base 47. Opposite end 48 of shaft 44 passes through the second shaft housing 73 of housing 33, brush plate seal 49 and is attached to first semi brush plate 50. First semi brush plate 50 is directly attached to first semi brush head 51. Shaft 45 extends in opposite directions from its attachment to Second semi gear wheel 43, as shown in FIG. 17. The second rotating anchor end 52, of shaft 45, rest in extended housing base 53, as shown in FIG. 17. Opposite end 54 of shaft 45 passes through the first shaft housing 72 of housing 33, brush plate seal 49 and is attached to second send brush plate 55. Second send brush plate 55 is directly attached to second semi brush head 56.

Guide rod 40 further comprises a second posh-pub rod 77. Second push-pull rod 77 is attached to the first free end of geared shaft 41. Second push-pull rod 77 comprises a vertical passage housing 57, as shown in FIG. 15. In FIG. 17 vertical passage housing 57 is shown receiving one end of male guide rod 58 and is secured by first retaining end 59 and second retaining end 60 respectively while the opposite end 61 of male guide rod 58 passes through shaft housing 74 of housing 33, bellows expansion seal 62 and is attached to brush plate 63. Brush plate 63 is directly attached to brush bead 64. Second push-pull rod 77 further comprises genie rod end 65. Guide rod end 65, as shown in FIG. 15 rest within guide rod end housing 66 which includes internal air vent 67 and internal, air vent 68 respectively, as shown in FIG. 15.

Figure 18:
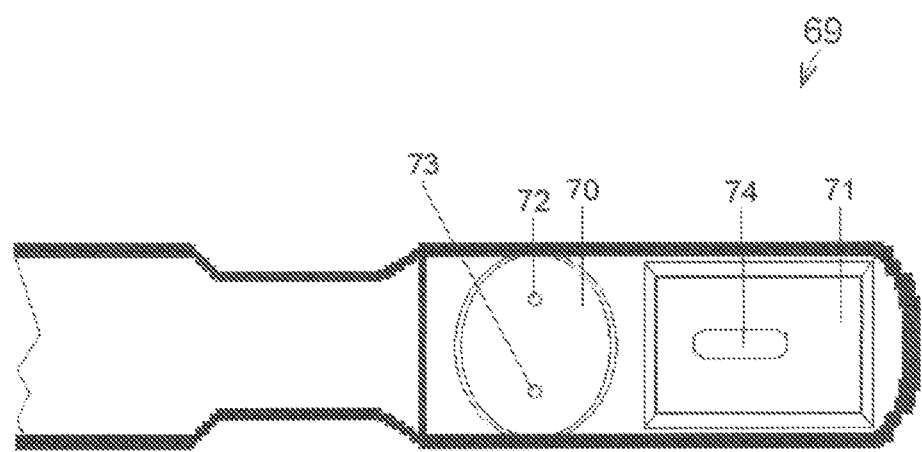
FIG. 18 is a top view of the upper electric toothbrush assembly.
Figure 19:
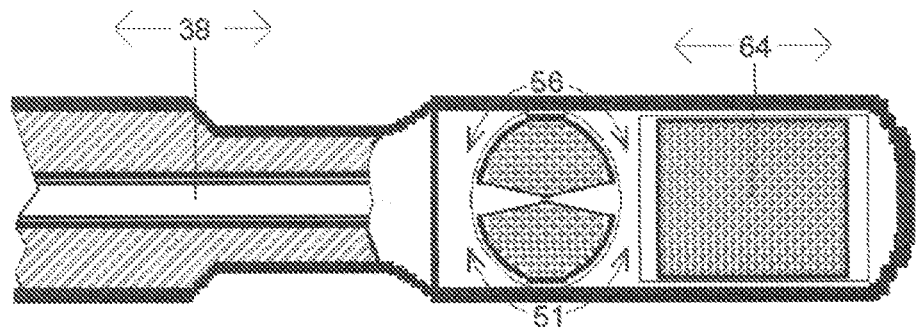
FIG. 19 is a top partial cross-sectional view of the upper electric toothbrush assembly.

A first electric toothbrush assembly 36 further comprises upper outer shell 69, as shown in FIG. 18. Upper outer shell 69 provides and first embedded platform 70 and second embedded platform 71. First embedded platform 76 is shaped well enough to allow brush plate seal 49, not shown, to snugly rest within its boundaries while establishing a border for first semi brush head 51 and 56, not shown. First embedded platform 70 further comprises first shaft housing 72 and second shaft housing 73. Second embedded platform 71 in the shape of a rectangle is allows the bellows expansion seal 62, not shown, to snugly rest within its boundaries while establishing a border for brush head 64, not shown. Second embedded platform 71 further comprises a shaft housing 74 designed to permit male guide rod 58 to move about freely. In FIG. 19 the directional arrows depict the movement of the reciprocating push-pull rod 38, first semi brush head 51, second semi brush head 56 and brush head 64 when in operation.

The motor 31 is driven by one or more batteries 75, as shown in FIG. 9. Motor 31 may be powered by a battery pack, which may be of the lithium-ion type for ready charging via a secondary voltage coil and an integral male socket portion within housing 33, not shown. Said male socket portion is detachably received in a corresponding female socket portion provided in a charger base assembly having a primary charging coil, also not shown. The electrical circuit would be defined with one side of the secondary coil attached to a negative battery terminal connector and the other side of the secondary coil coupled through a diode to the positive battery terminal. The diode rectifies voltage outputs from the coil, also not shown. Other prior art charging circuitry may be used. First electric toothbrush assembly 30 further comprises an end cap 78, as shown in FIG. 9. End cap 78 enables easy replacement of one or more batteries 75. Motor 31 is controlled by an on-off switch 76.

In operation, the user starts the DC motor 31 by moving the on-off switch 76 to the on position. As the cylindrical wheel 35 that is mounted on rotatable motor shaft 34 is rotated by the DC motor 31, the cam follower pin 37 follows the groove of the embedded cam groove track 36 to produce the desired back and forth motion of the reciprocating push-pull rod 38. The shape of the embedded cam groove track 36 defines the distance that the reciprocating push-pull rod 38 and the attached guide rod 40 travels back and forth.

Figure 11:
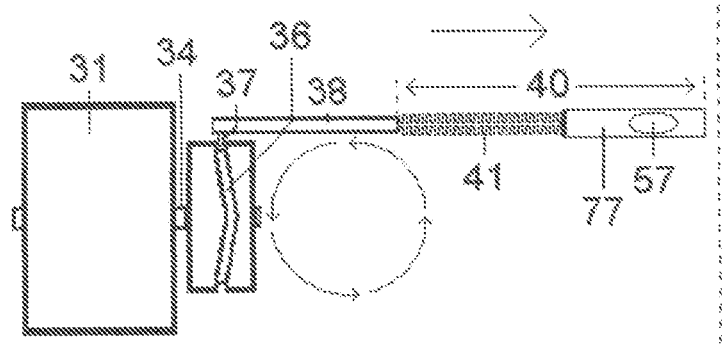
FIG. 11 is a second progressive view of a reciprocating drive mechanism of the electric tooth brush assembly in operation.
Figure 12:
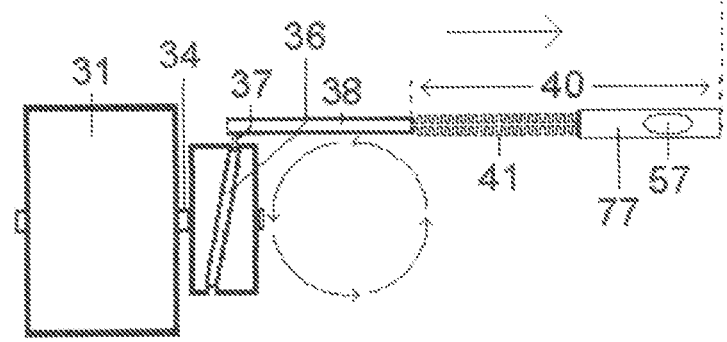
FIG. 12 is a third progressive view of a reciprocating drive mechanism of the electric toothbrush assembly in operation.
Figure 13:
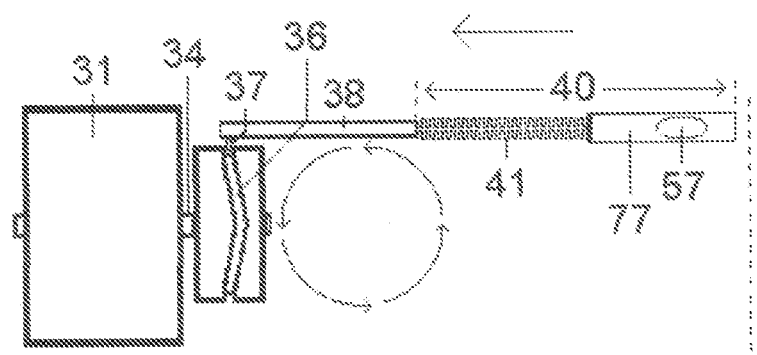
FIG. 13 is a fourth progressive view of a reciprocating drive mechanism of the electric toothbrush assembly in operation.
Figure 14:
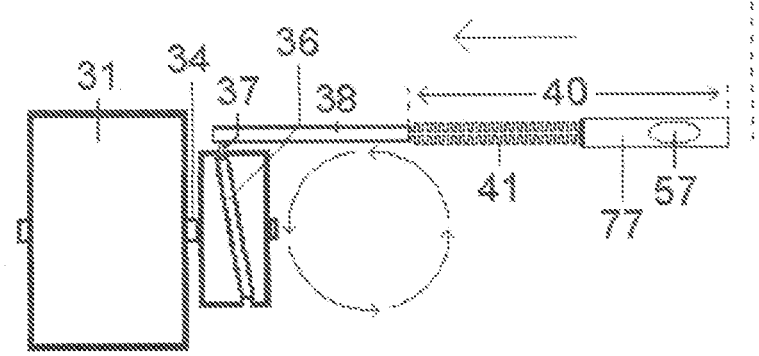
FIG. 14 is a fifth progressive view of a reciprocating drive mechanism of the electric toothbrush assembly in operation.

A partial progressive sequence of events illustrating one complete cycle of the reciprocating drive mechanism for an electric toothbrush assembly 30 of the type shown in FIG. 9 is shown in FIGS. 10, 11, 12, 13 and 14. In FIGS. 10, 11, 12, 13 and 14 DC motor 31 is rotating the rotatable motor shaft 34 counterclockwise. In FIG. 10 the embedded cam groove track 36 is at its closest point to casing surface of DC motor 31. As the rotatable motor shaft 34 rotates counterclockwise the cam follower pin 37 follows the groove of the embedded cam groove track 36 and causes the reciprocating push-pull rod 38 and the attached guide rod 40 to travel forth, as shown in FIG. 11 until it reaches the furthest forward plotted distance of the reciprocating push-pull rod 38 and the attached guide rod 40, as shown in FIG. 12. As the rotatable motor shaft 34 continues to rotate the direction of the reciprocating push-pull rod 38 and the attached guide rod 40 is changed to the opposite or back direction, as shown in FIG. 13, until it reaches that point where once again the embedded cam groove track 36 is at its closest point to casing surface of DC motor 31, as shown in FIG. 14. This cycle is continually repeated until the on-off switch 76 is moved by the user to the off position. The short back and forth movement of guide rod 40 engages first semi gear wheel 42 and 43 causing the movement of the first semi brush head 51, second semi brush head 56 in the direction shown in FIG. 19 while simultaneously pushing and pulling male guide rod 58 which ultimately moves brush head 64 in the direction shown in FIG. 19.

Figure 20:
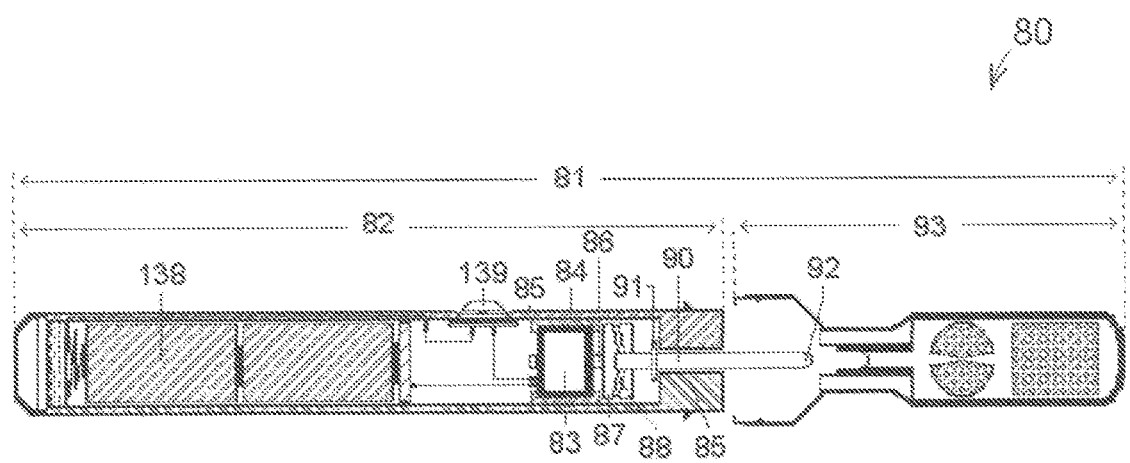
FIG. 20 is a cross-sectional top view of the electric toothbrush assembly having a detachable head where said detachable head is detached and further includes a reciprocating drive mechanism according to an embodiment of the invention.
Figure 22:
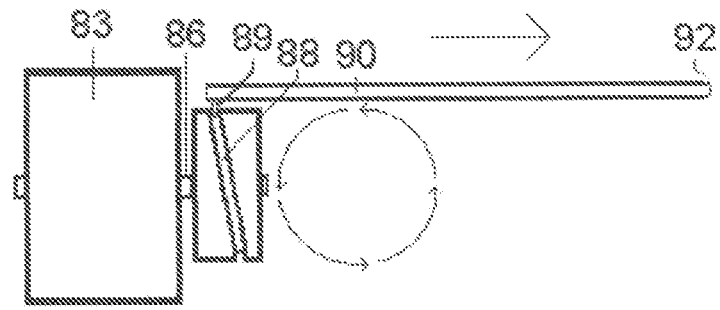
FIG. 22 is a first progressive view of the reciprocating drive mechanism of the electric toothbrush assembly having a detachable head in operation.

In FIG. 20 the second electric toothbrush assembly 80 comprises housing 81. Housing 81 comprises handle portion 82. Handle portion 82 comprises DC motor 83 encased in a motor housing 84. Motor housing 84 is embedded in housing 85. The DC motor 83 includes rotatable motor shaft 86 on which cylindrical wheel 87 is attached. The cylindrical wheel 87 has an embedded cam groove track 88 in which a cam follower pin 89 is loosely seated, as shown in FIG. 22. The cam follower pin 89 is attached to a reciprocating push-pull rod 90, as shown in FIG. 22. A portion of the reciprocating push-pull rod 90 is constrained by a portion of housing 85 thereby constraining the movement of the entire reciprocating push-pull rod 90, as shown in FIG. 20. A flat circular stop limiter 91 is attached to the reciprocating push-pull rod 90. Tapered male end 92 is attached at the other end of reciprocating push-pull rod 90 to that to which the cam follower pin 89 is attached, as shown in FIG. 20.

Figure 21:
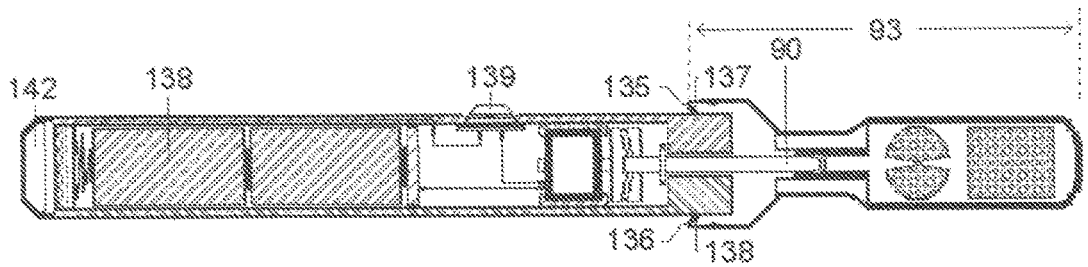
FIG. 21 is a cross-sectional top view of the electric toothbrush assembly having a detachable head where said detachable head is attached and further includes a reciprocating drive mechanism according to an embodiment of the invention.

Housing 81 further comprises a detachable brush head 93, as shown in FIGS. 20, 21 and 27. Detachable brush head 93 comprises rod 94 having female end 95, as shown in FIG. 27. At female end 95 of rod 94 is attached rod limber 96. Rod limiter 96 and a portion of rod 94 are constrained by housing 97 thereby constraining the entire rod 94. Guide rod 98 is attached at the other end of rod 94 to that to which the female end 95 is attached, as shown in FIG. 27. Guide rod 98 comprises a geared shaft 99 which simultaneously engages first semi gear wheel 100 and second semi gearwheel 101. First semi gear wheel 100 and 101 is attached to first shaft 102 and second shaft 103 respectively, as shown in FIG. 27. First shaft 102 extends in opposite directions from its attachment to first semi gear wheel 100, as shown in FIG. 28. First rotating anchor end 104 of first shaft 102 rest in extended housing base 105. Opposite end 100 of first shaft 102 passes through the second shaft housing 133 of housing 97, brush plate seat 107 and is attached to first semi brush plate 108. First semi brush plate 108 is directly attached to first semi brush head 109. Second shaft 103 extends in opposite directions from its attachment to Second semi gear wheel 101, as shown in FIG. 29. The second rotating anchor end 110, of second shaft 103, rests in extended housing base 111, as shown in FIG. 29. Opposite end 112 of second shaft 103 passes through the first shaft housing 132 of housing 97, brush plate seal 107 and is attached to second semi brush plate 113. Second semi brush plate 113 is directly attached to second semi brush head 114. Guide rod 98 further comprises a second push-pull rod 141. Second push-pull rod 141 is attached to the last free end of geared shaft 99. Second push-pull rod 41 comprises a vertical passage housing 115, as shown in FIG. 27. In FIG. 29 vertical passage housing 115 is shown receiving one end of male guide rod 116 and is secured by first retaining end 117 and second retaining end 118 respectively while the opposite end 119 of male guide rod 119 passes through shaft housing 134 of housing 97, bellows expansion seal 120 and is attached to brush plate 121. Brush plate 121 is directly attached to brush bead 122. Second push-pull rod 141 further comprises guide rod end 123. Guide rod end 123, as shown in FIG. 27 rest within guide rod end housing 124 which includes internal air vent 125 and internal air vent 126 respectively, as shown in FIG. 27. Guide rod end 123 is in continual contact with one side of movable plate 127 at all times due to the pressure exerted by spring 128 on the opposite side of movable plate 127. Movable plate is retained within guide reel end housing 124, as shown in FIG. 27.

Figure 30:
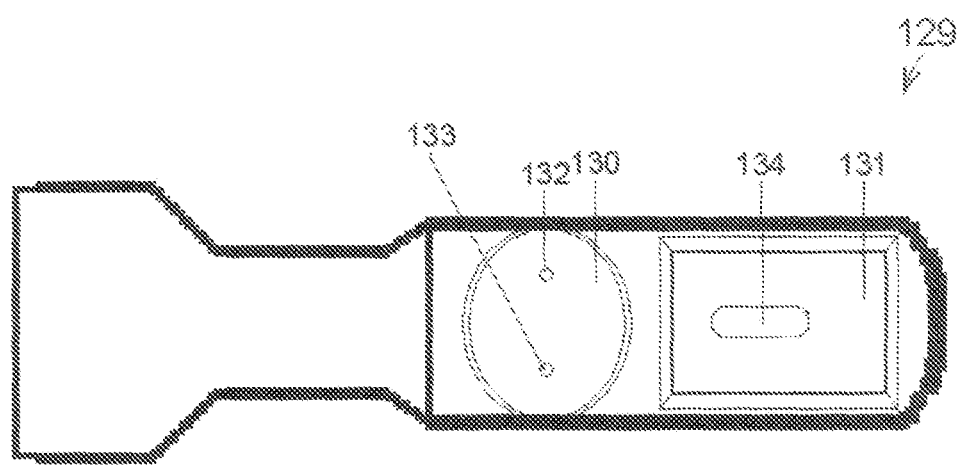
FIG. 30 is a top view of the upper electric toothbrush having a detachable head assembly.
Figure 31:
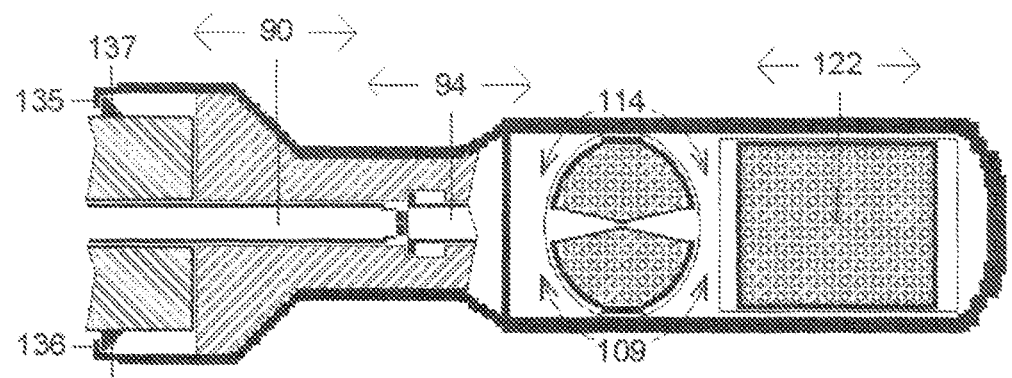
FIG. 31 is a top partial cross-sectional view of the upper electric toothbrush having a detachable head assembly.

A detachable brush head 95 further comprises upper carter shell 129, as shown in FIG. 30. Upper outer shell 129 provides and first embedded platform 130 and second embedded platform 131 first embedded platform 130 is shaped well enough to allow brush plate seal 107, not shown, to snugly rest within its boundaries while establishing a border for first semi brush head 169 and see end send brush head 114, not shown. First embedded platform 130 further comprises first shaft housing 132 and second shaft housing 133. Second embedded platform 131 in the shape of a rectangle is allows the bellows expansion seal 120, not shown, to snugly rest within its boundaries while establishing a border for brush head 122, not shown. Second embedded platform 131 further comprises a shaft housing 134 designed to permit male guide rod 116 to move about freely. In FIG. 31 the directional arrows depict the movement of the reciprocating push-pull rod 90, rod 94, first semi brush head 109, second semi brush head 114 and brush head 122 when in operation. The detachable brush head 93 is held in place by retaining clip end 135 and 136 are engaged with retaining clip anchor 137 and 138 respectively as shown in FIGS. 21 and 31.

The DC motor 83 is driven by one or more batteries 139, as shown in FIG. 20. DC motor 83 may be powered by a battery pack, which may be of the lithium-ion type for ready charging via a secondary voltage coil and an integral male socket portion within housing 35, not shown. Said male socket portion is detachably received in a corresponding female socket portion provided in a charger base assembly having a primary charging coil, also not shown. The electrical circuit would be defined with one side of the secondary coil attached to a negative battery terminal connector and the other side of the secondary coil coupled through a diode to the positive battery terminal. The diode rectifies voltage outputs from the coil, also not shown. Other prior art charging circuitry may be used. Second electric toothbrush assembly 80 further comprises an end cap 142, as shown in FIG. 21. End cap 142 enables easy replacement of one or more batteries 139. DC motor 83 is controlled by an on-off switch 140.

In operation, the user starts the DC motor 83 by moving the on-off switch 140 to the on position. As the cylindrical wheel 87 that is mounted on rotatable motor shaft 86 is rotated by the DC motor 83, the cam follower pin 89 follows the groove of the embedded cam groove track 88 to produce the desired back and forth motion of the reciprocating push-pull rod 90. The shape of the embedded cam groove track 88 defines the distance that the reciprocating push-pull rod 90 travels back and forth. The tapered male end 92 of reciprocating push-pull rod 90 is firmly pressed against female end 95 of rod 94 and as the reciprocating push-pull rod 90 travels back and forth so does rod 94 and the attached guide rod 98. Guide rod end 123 pushes movable plate 127 forth compressing spring 128. Compressed spring 128 continually pushes movable plate 127 against guide rod end 123 and eliminates any backlash.

Figure 23:
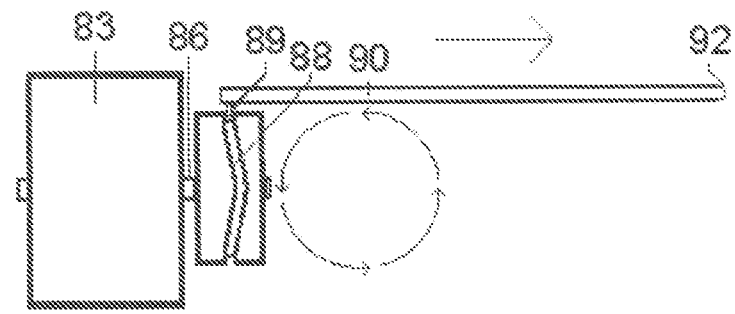
FIG. 23 is a second progressive view of a reciprocating drive mechanism of the electric toothbrush assembly having a detachable head in operation.
Figure 24:
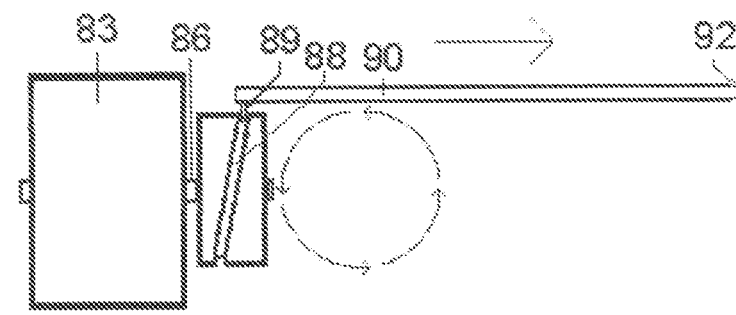
FIG. 24 is a third progressive view of a reciprocating drive mechanism of the electric toothbrush assembly having a detachable head in operation.
Figure 25:
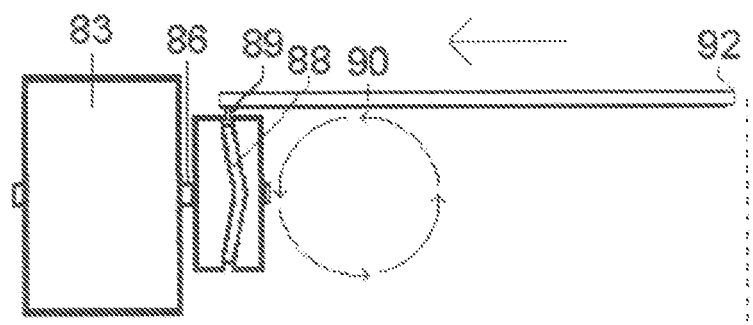
FIG. 25 is a fourth progressive view of a reciprocating drive mechanism of the electric toothbrush assembly having a detachable head in operation.
Figure 26:
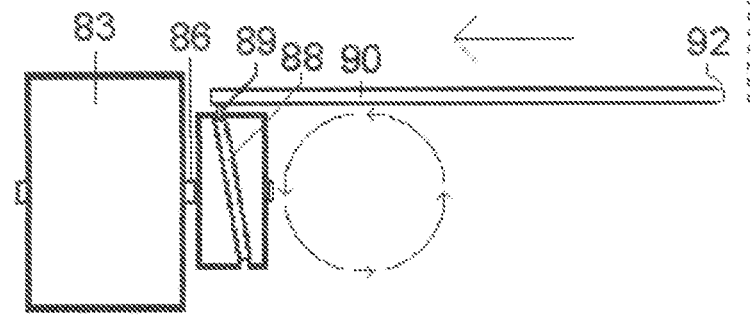
FIG. 26 is a fifth progressive view of a reciprocating drive mechanism of the electric toothbrush assembly having a detachable head in operation.

A partial progressive sequence of events illustrating one complete cycle of the reciprocating drive mechanism for a second electric toothbrush assembly 80 of the type shown in FIG. 20 is shown in FIGS. 22, 23, 24, 25 and 26. In FIGS. 22, 23, 24, 25 and 26 DC motor 83 is rotating the rotatable motor shaft 86 counterclockwise. In FIG. 22 the embedded cam groove track 88 is at its closest point to casing surface of DC motor 83. As the rotatable motor shaft 86 rotates counterclockwise the cam follower pin 89 follows the groove of the embedded cam groove track 88 and causes the reciprocating push-pull rod 90 and the attached guide rod 98 to travel forth, as shown in FIG. 23 until it reaches the furthest forward plotted distance of the reciprocating push-pull rod 90 and the attached guide rod 98, as shown in FIG. 24 As the rotatable motor shaft 86 continues to rotate the direction of the reciprocating push-pull rod 90 and the attached guide rod 98 is changed to the opposite or back direction, as shown in FIG. 25, until it reaches that point where once again the embedded cam groove track 88 is at its closest point to casing surface of DC motor 83, as shown in FIG. 26. This cycle is continually repeated until the on-off switch 140 is moved by the user to the off position. The short back and forth movement of guide rod 98 engages first semi gear wheel 100 and 101 causing the movement of the first semi brush head 109, second semi brush head 114 in the direction shown in FIG. 31 while simultaneously pushing and pulling male guide rod 116 which ultimately moves brush head 122 in the direction shown in FIG. 31.

While the present invention has been described and illustrated above in the content of an electric mascara applicator assembly and a reciprocating drive mechanism; and in the context of a first electric toothbrush assembly and a reciprocating drive mechanism, and in the context of a second electric toothbrush assembly and a reciprocating drive mechanism having a device for converting a rotating motion into a reciprocating motion it is not to be considered limited to either of these assemblies. It is to be understood that other embodiments maybe used or modifications and additions may be made to the described embodiments for performing the same function of the present invention without deviating therefrom. Therefore, the present invention should be construed in breadth and scope in accordance with the recitation of the appended claims.

What is claimed is:

1. A device for converting a rotating motion into a reciprocating motion comprising:
   a housing;
   a motor with a rotatable motor shaft;
   a cylindrical component having an embedded cam groove track therein attached in a piggyback manner onto said rotatable motor shaft;
   a rod component constrained to travel back and forth;
   a cam follower carried on said rod component engaged in said embedded cam groove track of said cylindrical component so that as said rotatable motor shaft rotates, said cam follower transmits the movement dictated by said embedded cam groove track to said rod component thereby causing said rod component to travel back and forth once for each rotation of said rotatable motor shaft; and
   an expandable seal simultaneously seated on said rod component and said housing.

2. A device according to claim 1, wherein said cylindrical component has said embedded cam groove track set into the curved surface of said cylindrical component.

3. A device according to claim 1, wherein said embedded cam groove track in said cylindrical component has a defined shape to receive said cam follower.

4. A device according to claim 1, further comprising a circular stop limiter set on said rod component.

5. A device according to claim 1, further comprising at least one battery to power rotation for said rotatable motor shaft.

6. An electric mascara applicator assembly comprising a device for converting a rotating motion into a reciprocating motion as set forth in claim 1 further including a brush head element attached to said rod component.

7. An electric mascara applicator assembly according to claim 6, further comprising a battery compartment which is embedded in said housing having a removable negative battery contact held firmly in place by an end cap.

8. An electric mascara applicator assembly according to claim 6, wherein said housing constrains said rod component.

9. An electric mascara applicator assembly according to claim 6, wherein said housing further comprises a tube to constrain said rod component.

10. An electric mascara applicator assembly according to claim 6, further comprising an off center weight attachable to a first free end of said rotatable motor shaft.

11. An electric mascara applicator assembly according to claim 6, further comprising a DC motor a battery power source and a switching means disposed in said housing between said battery power source and said DC motor whereby said switching means selectively electrically connects or disconnects said battery power source with said DC motor.

12. An electric mascara applicator assembly according to claim 6, further comprising at least one air flow vent.

13. An electric mascara applicator assembly according to claim 6, further comprising a detachable container comprising a chamber having an opening and a surface stripper having an opening wherein said opening of said chamber is disposed on one end of said detachable container, said opening of said chamber communicating with said opening of said surface stripper within said opening of said chamber wherein as said brush head element is removed from said detachable container said brush head element first passes through said opening of said surface stripper where said brush head element brushes or rubs against the wall of said opening of said surface stripper thereby removing and distributing a cosmetic product evenly upon said brush head element and then passes through said opening of said chamber.

14. An electric toothbrush assembly comprising a device for converting a rotating motion into a reciprocating motion as set forth in claim 1 further including at least one back and forth reciprocating brush head and at least one opposite semi-circular reciprocating brush head.

15. An electric toothbrush assembly according to claim 14, further comprising a guide rod having a geared shaft, a reciprocating push-pull rod affixed to said guide rod, a first semi gear wheel and a second semi gear wheel engaged with said geared shaft of said guide rod.

16. An electric toothbrush assembly according to claim 14, wherein said guide rod having said geared shaft engaged with said first semi gear wheel and said second semi gear wheel enables a back and forth partial rotational movement of said at least one opposite semi-circular reciprocating brush head.

17. An electric toothbrush assembly comprising a device for converting a rotating motion into a reciprocating motion as set forth in claim 1 further including a detachably connected back and forth reciprocating brush head and at least one opposite semi-circular reciprocating brush head.

* * * * *